(12) United States Patent
Askem et al.

(10) Patent No.: US 11,123,471 B2
(45) Date of Patent: Sep. 21, 2021

(54) NEGATIVE PRESSURE WOUND THERAPY DEVICE CONTROL IN PRESENCE OF FAULT CONDITION

(71) Applicant: Smith & Nephew PLC, Watford (GB)

(72) Inventors: Ben Alan Askem, Leeds (GB);
Yeswanth Gadde, Hedon (GB);
William Kelbie, Inverness (GB);
Damyn Musgrave, Cottenham (GB);
Felix Clarence Quintanar, Hull (GB);
Daniel Lee Steward, Hull (GB)

(73) Assignee: Smith & Nephew PLC, Watford (GB)

( * ) Notice: Subject to any disclaimer, the term of this patent is extended or adjusted under 35 U.S.C. 154(b) by 99 days.

(21) Appl. No.: 16/491,742

(22) PCT Filed: Mar. 8, 2018

(86) PCT No.: PCT/EP2018/055698
§ 371 (c)(1),
(2) Date: Sep. 6, 2019

(87) PCT Pub. No.: WO2018/162613
PCT Pub. Date: Sep. 13, 2018

(65) Prior Publication Data
US 2021/0128799 A1    May 6, 2021

Related U.S. Application Data

(60) Provisional application No. 62/468,796, filed on Mar. 8, 2017.

(51) Int. Cl.
*A61M 1/00* (2006.01)

(52) U.S. Cl.
CPC ............ *A61M 1/742* (2021.05); *A61M 1/743* (2021.05); *A61M 1/962* (2021.05);
(Continued)

(58) Field of Classification Search
CPC .. A61M 1/0033; A61M 1/009; A61M 1/0035; A61M 2205/502; A61M 2205/13; A61M 2205/3344
(Continued)

(56) References Cited

U.S. PATENT DOCUMENTS

| 3,874,387 A | 4/1975 | Barbieri |
| 4,224,941 A | 9/1980 | Stivala |

(Continued)

FOREIGN PATENT DOCUMENTS

| CN | 201664463 U | 12/2010 |
| CN | 203490495 U | 3/2014 |

(Continued)

OTHER PUBLICATIONS

International Search Report and Written Opinion, re PCT Application No. PCT/EP2018/055698, dated Apr. 30, 2018.
(Continued)

*Primary Examiner* — Andrew J Mensh
*Assistant Examiner* — Nhu Q. Tran
(74) *Attorney, Agent, or Firm* — Knobbe, Martens, Olson & Bear, LLP

(57) ABSTRACT

Embodiments of negative pressure wound therapy systems and methods are disclosed. In one embodiment, an apparatus includes a wound dressing, negative pressure source, switch, interface element, and control circuitry. The negative pressure source, switch, and interface element can be disposed on or within the wound dressing. The control circuitry can be in a first or second mode. In the first mode, the control circuitry can cause supply of negative pressure in response to a first user input via the switch when the negative pressure source is not supplying negative pressure and prevent supply of negative pressure in response to the first user input while the negative pressure source is supplying negative pressure, (Continued)

and the control circuitry can change from the first mode to a second mode in response to a second user input via the interface element. In the second mode, the control circuitry can disable supply of negative pressure.

20 Claims, 12 Drawing Sheets

(52) U.S. Cl.
CPC . *A61M 2205/13* (2013.01); *A61M 2205/3344* (2013.01); *A61M 2205/502* (2013.01)

(58) Field of Classification Search
USPC ........................................................ 604/319
See application file for complete search history.

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,636,010 B1 | 10/2003 | Malmstrom et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| D625,422 S | 10/2010 | Arbesman et al. |
| 7,815,616 B2 | 10/2010 | Boehringer et al. |
| 7,837,673 B2 | 11/2010 | Vogel |
| 7,846,141 B2 | 12/2010 | Weston |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,080,702 B2 | 12/2011 | Blott et al. |
| 8,092,441 B2 | 1/2012 | Sugito |
| 8,158,844 B2 | 4/2012 | Mcneil |
| 8,167,869 B2 | 5/2012 | Wudyka |
| 8,212,100 B2 | 7/2012 | Moore |
| 8,215,929 B2 | 7/2012 | Shen et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,500,776 B2 | 8/2013 | Ebner |
| 8,529,548 B2 | 9/2013 | Blott et al. |
| 8,545,466 B2 | 10/2013 | Andresen et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,641,691 B2 | 2/2014 | Fink et al. |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,870,837 B2 | 10/2014 | Locke et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,265,665 B2 | 2/2016 | Robinson et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,560,975 B2 | 2/2017 | Mei et al. |
| D787,690 S | 5/2017 | Mackay et al. |
| 9,770,368 B2 | 9/2017 | Robinson et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,016,544 B2 | 7/2018 | Coulthard et al. |
| 10,046,095 B1 | 8/2018 | Middaugh et al. |
| 10,046,096 B2 | 8/2018 | Askem et al. |
| 10,086,117 B2 | 10/2018 | Locke et al. |
| 2003/0212357 A1 | 11/2003 | Pace |

(56) References Cited

U.S. PATENT DOCUMENTS

| | | |
|---|---|---|
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0055209 A1 | 3/2007 | Patel et al. |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2007/0265586 A1 | 11/2007 | Joshi et al. |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2009/0240218 A1 | 9/2009 | Braga et al. |
| 2010/0022990 A1 | 1/2010 | Karpowicz et al. |
| 2010/0042074 A1 | 2/2010 | Weston et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2010/0307496 A1* | 12/2010 | Lueckenhoff ...... B65H 75/4484 128/204.18 |
| 2011/0092927 A1 | 4/2011 | Wilkes et al. |
| 2011/0112492 A1 | 5/2011 | Bharti et al. |
| 2011/0224631 A1 | 9/2011 | Simmons et al. |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0215638 A1 | 8/2013 | Dabov et al. |
| 2014/0100536 A1 | 4/2014 | Angel |
| 2014/0343518 A1 | 11/2014 | Riesinger |
| 2015/0025482 A1 | 1/2015 | Begin et al. |
| 2015/0057625 A1 | 2/2015 | Coulthard |
| 2015/0174304 A1* | 6/2015 | Askem ............... A61M 1/0027 604/319 |
| 2015/0202354 A1 | 7/2015 | Wall |
| 2016/0015873 A1 | 1/2016 | Robinson et al. |
| 2016/0166438 A1 | 6/2016 | Rovaniemi |
| 2016/0199546 A1 | 7/2016 | Chao |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0319761 A1 | 11/2017 | Locke et al. |
| 2017/0326277 A1 | 11/2017 | Huang |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0272052 A1 | 9/2018 | Locke et al. |
| 2018/0296397 A1 | 10/2018 | Askem et al. |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0125943 A1 | 5/2019 | Askem et al. |
| 2019/0142644 A1 | 5/2019 | Askem et al. |
| 2019/0143007 A1 | 5/2019 | Askem et al. |
| 2019/0159938 A1 | 5/2019 | Askem et al. |
| 2019/0192350 A1 | 6/2019 | Gowans et al. |
| 2019/0282737 A1 | 9/2019 | Beadle et al. |
| 2020/0022846 A1 | 1/2020 | Beadle et al. |

FOREIGN PATENT DOCUMENTS

| | | |
|---|---|---|
| DE | 19844355 A1 | 4/2000 |
| EP | 0512543 A2 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2326295 A1 | 6/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |

(56) References Cited

FOREIGN PATENT DOCUMENTS

| | | |
|---|---|---|
| EP | 2861869 B1 | 7/2016 |
| EP | 2945584 B1 | 7/2016 |
| EP | 2293749 B1 | 8/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 2249761 B1 | 4/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2781208 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 2687241 B2 | 11/2018 |
| EP | 2687243 B2 | 11/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2939320 A1 | 6/2010 |
| GB | 2511523 A | 9/2014 |
| JP | H04354722 A | 12/1992 |
| RU | 131622 U1 | 8/2013 |
| WO | WO-2009098696 A2 | 8/2009 |
| WO | WO-2009120951 A2 | 10/2009 |
| WO | WO-2011130570 A1 | 10/2011 |
| WO | WO-2011135285 A1 | 11/2011 |
| WO | WO-2011144888 A1 | 11/2011 |
| WO | WO-2014099709 A1 | 6/2014 |
| WO | WO-2016126560 A1 | 8/2016 |
| WO | WO-2017079174 A1 | 5/2017 |
| WO | WO-2017196888 A1 | 11/2017 |
| WO | WO-2018056060 A1 | 3/2018 |
| WO | WO-2018115461 A1 | 6/2018 |
| WO | WO-2018156730 A1 | 8/2018 |
| WO | WO 2018/162613 | 9/2018 |
| WO | WO-2018158250 A1 | 9/2018 |
| WO | WO-2018164803 A1 | 9/2018 |
| WO | WO-2018185138 A1 | 10/2018 |
| WO | WO-2018192978 A1 | 10/2018 |
| WO | WO-2018206420 A1 | 11/2018 |
| WO | WO-2019053101 A1 | 3/2019 |
| WO | WO-2019053106 A1 | 3/2019 |
| WO | WO-2019086332 A1 | 5/2019 |
| WO | WO-2019086341 A1 | 5/2019 |
| WO | WO-2019086475 A1 | 5/2019 |
| WO | WO-2019193141 A1 | 10/2019 |

OTHER PUBLICATIONS

International Preliminary Report on Patentability for Application No. PCT/EP2018/055698, dated Sep. 19, 2019, 7 pages.

* cited by examiner

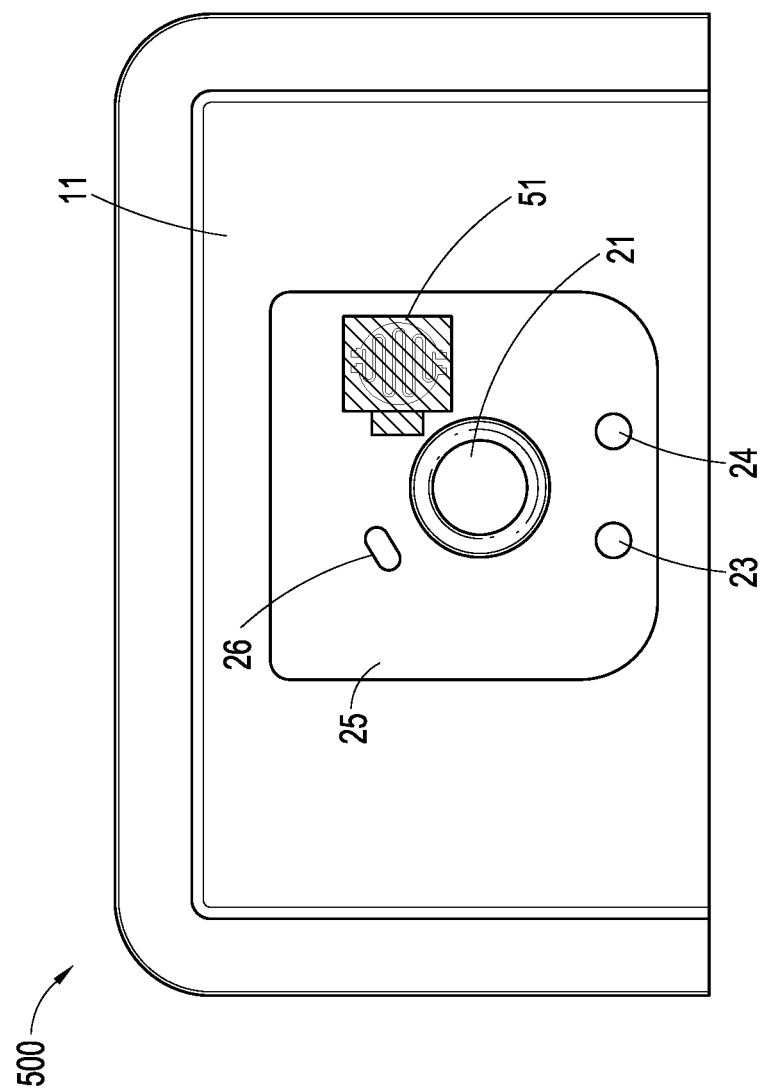

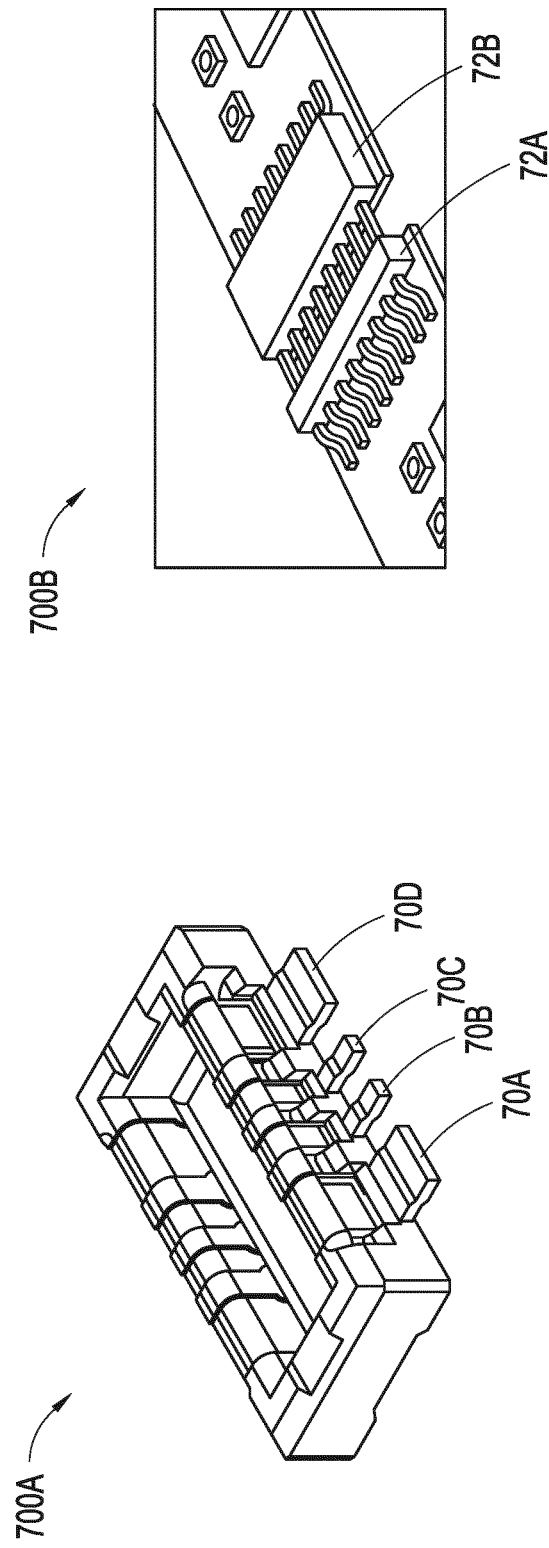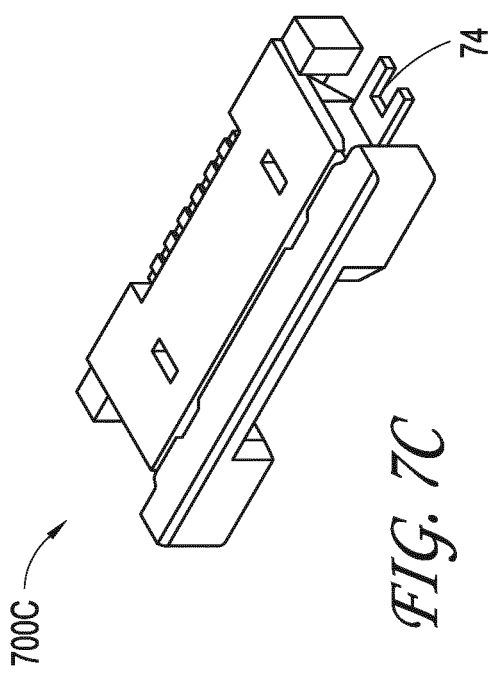
FIG. 7B
FIG. 7C
FIG. 7A

NEGATIVE PRESSURE WOUND THERAPY DEVICE CONTROL IN PRESENCE OF FAULT CONDITION

CROSS-REFERENCE TO RELATED APPLICATIONS

This application is a U.S. national stage application of International Patent Application No. PCT/EP2018/055698, filed Mar. 8, 2018, which claims the benefit of U.S. Provisional Application No. 62/468,796, filed Mar. 8, 2017; the disclosure of which is hereby incorporated by reference in its entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound is disclosed. The apparatus can include: a wound dressing configured to be placed over a wound of a patient; a negative pressure source disposed on or within the wound dressing, the negative pressure source configured to provide negative pressure to the wound dressing via a fluid flow path; a switch disposed on or within the wound dressing, the switch being configured to receive a first user input; an interface element disposed on or within the wound dressing, the interface element being configured to receive a second user input; and control circuitry. The control circuitry can be electrically coupled to the switch and the interface element. When in a first mode, the control circuitry can: supply of negative pressure with the negative pressure source in response to receipt of the first user input while the negative pressure source is not supplying negative pressure, prevent supply of negative pressure with the negative pressure source in response to receipt of the first user input while the negative pressure source is supplying negative pressure, and change from the first mode to a second mode different from the first mode in response to receipt of the second user input. When in a second mode, the control circuitry can disable supply of negative pressure with the negative pressure source.

The apparatus of the preceding paragraph can include one or more of the following features: When the switch experiences a fault and is no longer able to receive the first user input, the control circuitry can prevent or disable supply of negative pressure with the negative pressure source in response to receipt of no user inputs other than the second user input. The control circuitry can supply of negative pressure with the negative pressure source in response to receipt of no user inputs other than the first user input. While the negative pressure source is supplying negative pressure, the control circuitry can prevent or disable supply of negative pressure with the negative pressure source in response to receipt of no user inputs other than the first user input and the second user input. When the control circuitry is in the second mode, the control circuitry can, in response to receipt of the second user input, change from the second mode to the first mode, and supply of negative pressure with the negative pressure source. The control circuitry can disable supply of negative pressure with the negative pressure source by deactivation of operation of the negative pressure source or the control circuitry, opening of a vent positioned in the fluid flow path, or closing of a valve positioned in the fluid flow path. The control circuitry can deactivate operation of the negative pressure source or the control circuitry by (i) disconnection of power to the negative pressure source or the control circuitry or (ii) withdrawal of an enable signal provided to the negative pressure source or the control circuitry. The control circuitry can prevent supply of negative pressure with the negative pressure source by deactivation of operation of the negative pressure source, opening of a vent positioned in the fluid flow path, and closing of a valve positioned in the fluid flow path. The interface element can be molded in film coupled to the wound dressing. The interface element can include an electrical contact configured to receive the second user input. The switch can receive the first user input in response to depression of the switch for a period of time. The period of time can be between 0.5 seconds and 5 seconds.

A method of operating, using, or manufacturing the apparatus of the preceding two paragraphs is also disclosed.

In some embodiments, a method of operating a negative pressure wound therapy apparatus comprising a wound dressing is disclosed. A negative pressure source can be disposed on or within the wound dressing, and a switch can be disposed on or within the wound dressing. An interface element can be disposed on or within the wound dressing, and the switch can receive a first user input and the interface element can receive a second user input. The method can include: supplying of negative pressure with the negative pressure source to the wound dressing via a fluid flow path in response to receipt of the first user input while the negative pressure source is not supplying negative pressure to the wound dressing; preventing supply of negative pressure with the negative pressure source to the wound dressing via the fluid flow path in response to receipt of the first user input while the negative pressure source is supplying negative pressure to the wound dressing; in response to receipt of the second user input, disabling supply of negative pressure with the negative pressure source to the wound dressing; and subsequent to said disabling supply of negative pressure, not supplying of negative pressure with the negative pressure source to the wound dressing via the fluid flow path in response to receipt of the first user input.

The method of the preceding paragraph can include one or more of the following features: The method can further include, subsequent to the switch experiencing a fault and no longer being able to receive the first user input, preventing or disabling supply of negative pressure with the negative pressure source in response to receipt of no user inputs other than the second user input. The method can further include supplying of negative pressure with the negative pressure source in response to receipt of no user inputs other than the first user input. The method can further include, while the negative pressure source is supplying negative pressure, preventing or disabling supply of negative pressure with the negative pressure source in response to receipt of no user inputs other than the first user input and the second user input. The disabling supply of negative pressure can include deactivation of operation of the negative pressure source or the control circuitry, opening of a vent positioned in the fluid flow path, or closing of a valve positioned in the fluid flow path. The method can further include receiving the second user input via an electrical contact of the interface element. The method can further include receiving the first user input in response to depression of the switch for a period of time. The period of time can be between 0.5 seconds and 5 seconds.

BRIEF DESCRIPTION OF THE DRAWINGS

Features and advantages of the present disclosure will be apparent from the following detailed description, taken in conjunction with the accompanying drawings of which:

FIGS. 3, 4, 5A, and 5B illustrate top views of negative pressure therapy systems according to some embodiments, such as the negative pressure therapy system of FIGS. 2A and 2B.

FIGS. 7A, 7B, and 7C illustrate connectors according to some embodiments.

DETAILED DESCRIPTION

Figure 1:
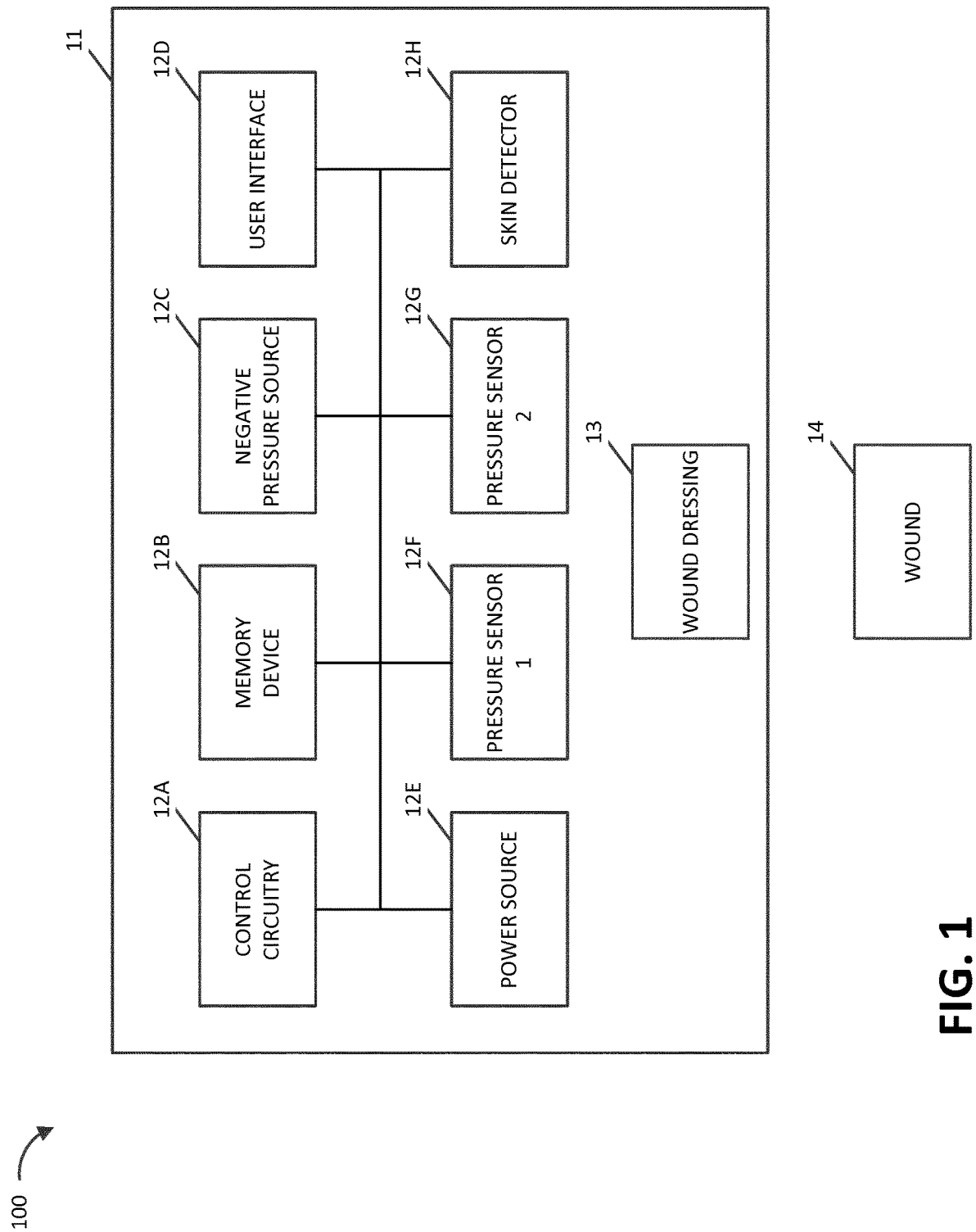
FIG. 1 illustrates a negative pressure therapy system according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Overview

The user interfaces of some TNP apparatuses may have a limited elements through which a user can provide user input. In some instances, particular user interfaces may include just a single element usable by the user to stop and start delivery of negative pressure, and the user may not be able to replace or interchange the single element with another element. These particular user interfaces can desirably be easier to construct and operate than more complicated user interfaces having numerous elements. However, the particular user interfaces may present a problem if the single element experiences a fault (for example, a failure) and is no longer able to function to receive user input. The user of the particular user interfaces may undesirably be unable to start delivery of negative pressure if negative pressure is not already being provided and stop delivery of negative pressure if negative pressure is being provided.

The situation of a user being unable to stop delivery of negative pressure can additionally introduce risks to the healing of a wound of a patient. If the patient experiences discomfort from the wound dressing during delivery of negative pressure and the single element experiences is no longer able to function to receive user input, the patient may be forced to remove the wound dressing to terminate delivery of negative pressure. The removal of the wound dressing can damage the wound of the patient and hinder any healing trajectory that was already progressed, as well as exposing the wound to external contaminants due to a loss of protection from the wound dressing.

To address the situation of the user being unable to stop delivery of negative pressure, a TNP apparatus with the single element usable by the user to stop and start delivery of negative pressure can include another mechanism, such as another redundant mechanism, to stop delivery of negative pressure. In some implementations, a header circuit with four circuits could be used, and each pair of circuits could be used to deactivate operation by one or more means. One pair of the circuit could be used to connect to a power supply of the TNP apparatus, and the other pair of circuits could be used to connect to an enable signal (for example, a control circuitry enable signal). Additionally or alternatively, a surface mount technology (SMT) pin header could be used. The another mechanism can, for instance, be an activating part molded in a film that may be welded to the wound dressing so that the activating mechanism may not be easily lost. Additionally or alternatively, the locking mechanism of a zero insertion force (ZIF) connector may be used to improve retention. The activating mechanism can, in another example, be a printed circuit board (PCB), such as a flexible PCB, built into a film for insertion. The activating mechanism can, in yet another example, include a conductive label that completes the circuit when attached and is removable to stop delivery of negative pressure. In some implementations, a tab may additionally or alternatively be used, and the tab may, for instance, be pulled to disrupt a power supply for the TNP apparatus (such as to remove a battery) or pulled to rip an aperture in the wound dressing (such as by pulling a tab on an outside of the wound dressing) to force a gross leak that causes termination of delivery of negative pressure.

Reduced Pressure Therapy Systems and Methods

FIG. 1 illustrates a negative pressure therapy system 100 that includes a TNP apparatus 11 and a wound 14. The TNP apparatus 11 can be used to treat the wound 14. The TNP apparatus 11 can include control circuitry 12A, memory 12B, a negative pressure source 12C, a user interface 12D, a power source 12E, a first pressure sensor 12F, a second pressure sensor 12G, and a skin detector 12H that are configured to electrically communicate with one another. In addition, the TNP apparatus 11 can include a wound dressing 13. The power source 12E can provide power to one or more components of the TNP apparatus 11.

One or more of the control circuitry 12A, memory device 12B, negative pressure source 12C, user interface 12D, power source 12E, first pressure sensor 12F, second pressure sensor 12G, and skin detector 12H can be integral with, incorporated as part of, attached to, or disposed in the wound dressing 13. The TNP apparatus 11 can accordingly be considered to have its control electronics and pump on-board the wound dressing 13 rather than separate from the wound dressing 13.

The control circuitry 12A can include one or more controllers, activation circuits, boost converters, current limiters, feedback conditioning circuits, and H-bridge inverters. The one or more controllers can control the operations of one or more other components of the TNP apparatus 11 according at least to instructions stored in the memory device 12B. The one or more controllers can, for instance, control operations of the negative pressure source 12C via a signal input (for example, a pulse width modulation of the signal) to the one or more H-bridge inverters, which in turn drive power from the power source 12E to the negative pressure source 12C.

The negative pressure source 12C can include a pump, such as, without limitation, a rotary diaphragm pump or other diaphragm pump, a piezoelectric pump, a peristaltic pump, a piston pump, a rotary vane pump, a liquid ring pump, a scroll pump, a pump operated by a piezoelectric transducer, a voice coil pump, or any other suitable pump or micropump or any combinations of the foregoing.

The user interface 12D can include one or more elements that receive user inputs or provide user outputs to a patient or caregiver. The one or more elements that receive user inputs can include buttons, switches, dials, touch screens, or the like, and the one or more elements that provide user outputs can include activation of a light emitting diode (LED) or one or more pixels of the display or activation of a speaker or the like. In one example, the user interface 12D can include a switch to receive a first user input (for instance, a negative pressure activation or deactivation input), an interface element to receive a second user input (for instance, a negative pressure disable input), and two LEDs to indicate an operating status (for example, functioning normally, under fault condition, or awaiting user input) of the TNP apparatus 11.

The first pressure sensor 12F can be used to monitor pressure underneath the wound dressing 13, such as pressure in a fluid flow path connecting the negative pressure source 12C and the wound 14, pressure at the wound 14, or pressure in the negative pressure source 12C. The second pressure sensor 12G can be used to monitor pressure external to the wound dressing 13. The pressure external to the wound dressing can be atmospheric pressure; however, the atmospheric pressure can vary depending on, for instance, an altitude of use or pressurized environment in which the TNP apparatus 11 may be used.

The control circuitry 12A can control the supply of negative pressure by the negative pressure source 12C according at least to a comparison between the pressure monitored by the first pressure sensor 12F and the pressure monitored by the second pressure sensor 12G. The control circuitry 12A can include a controller, such as a microcontroller or microprocessor.

The skin detector 12H can be used to determine if the wound dressing 13 has been placed over the wound 14. The skin detector 12H can, for example, detect skin of a patient. The detection by the skin detector 12H can confirm whether the wound dressing 13 is coupled to skin of the patient next to the wound 14. When skin is detected, this may indicate that activation of the TNP apparatus 11 is intentional rather than unintentional and can thus be used to prevent unintentional activation of the TNP apparatus 11 or an end-of-life timer of the TNP apparatus 11, such as during transportation or manufacture of the TNP apparatus 11. In one example, if the skin detector 12H indicates to the control circuitry 12A that skin is detected, the control circuitry 12A can activate the negative pressure source 12C to supply negative pressure in response to receiving an activation input via the user interface 12D. If the skin detector 12H, on the other hand, indicates to the control circuitry 12A that skin is not detected, the control circuitry 12A may not activate the negative pressure source 12C to supply negative pressure in response to receiving an activation input via the user interface 12D. The skin detector 12H can include one or more of a capacitive sensor, an impedance sensor, an optical sensor, a piezoresistive sensor, a piezoelectric sensor, an elastoresistive sensor, and an electrochemical sensor.

The wound dressing 13 can include a wound contact layer, a spacer layer, and an absorbent layer. The wound contact layer can be in contact with the wound 14. The wound contact layer can include an adhesive on the patient facing side for securing the dressing to the skin surrounding the wound 14 or on the top side for securing the wound contact layer to a cover layer or other layer of the wound dressing 13. In operation, the wound contact layer can provide unidirectional flow so as to facilitate removal of exudate from the wound while blocking or substantially preventing exudate from returning to the wound 14. The spacer layer can assist in distributing negative pressure over the wound site and facilitating transport of wound exudate and fluids into the wound dressing 13. Further, the absorbent layer can absorb and retain exudate aspirated from the wound 14.

The control circuitry 12A can, in some instances, prevent supply of negative pressure with the negative pressure source 12C. For example, the control circuitry 12A can prevent supply of negative pressure by deactivating operation of the negative pressure source, opening a vent positioned in the fluid flow path, and closing a valve positioned in the fluid flow path.

The supply of negative pressure with the negative pressure source 12C can, in some instances, be disabled. For example, supply of negative pressure can be disabled by deactivating operation of the negative pressure source 12C or the control circuitry 12A, opening a vent positioned in the fluid flow path, and closing a valve positioned in the fluid flow path. In some implementations, deactivating operation of the negative pressure source 12C or the control circuitry 12A can be performed by disconnection of power to the negative pressure source 12C or the control circuitry 12A or withdrawal of an enable signal provided to the negative pressure source 12C or the control circuitry 12A.

The control circuitry 12A can monitor a duty cycle of the negative pressure source 12C. As is used herein, the "duty cycle" can reflect the amount of time the negative pressure source 12C is active or running over a period of time. In other words, the duty cycle can reflect time that the negative pressure source 12C is in an active state as a fraction of total time under consideration. Duty cycle measurements can reflect a level of activity of the negative pressure source 12C. For example, the duty cycle can indicate that the negative pressure source 12C is operating normally, working hard, working extremely hard, etc. Moreover, the duty cycle measurements, such as periodic duty cycle measurements, can reflect various operating conditions, such as presence or severity of leaks, rate of flow of fluid (for instance, air, liquid, or solid exudate, etc.) aspirated from a wound, or the like. Based on the duty cycle measurements, such as by comparing the measured duty cycle with a set of thresholds (for instance, determined in calibration), the controller can execute or be programmed to execute algorithms or logic that control the operation of the system. For example, duty cycle measurements can indicate presence of a high leak, and the control circuitry 12A can be programmed to indicate this condition to a user (for instance, patient, caregiver, or physician) or temporarily suspend or pause operation of the source of negative pressure in order to conserve power.

When the TNP apparatus 11 may be used to treat the wound 14, the wound dressing 13 can create a substantially sealed or closed space around the wound 13 and under the wound dressing 13, and the first pressure sensor 12F can periodically or continuously measure or monitor a level of pressure in this space. The control circuitry 12A can control the level of pressure in the space between a first negative pressure set point limit and at least a second negative pressure set point limit. In some instances, the first set point limit can be approximately −70 mmHg, or from approximately −60 mmHg or less to approximately −80 mmHg or more. In some instances, the second set point limit can be approximately −90 mmHg, or from approximately −80 mmHg or less to approximately −100 mmHg or more.

Figure 2A:
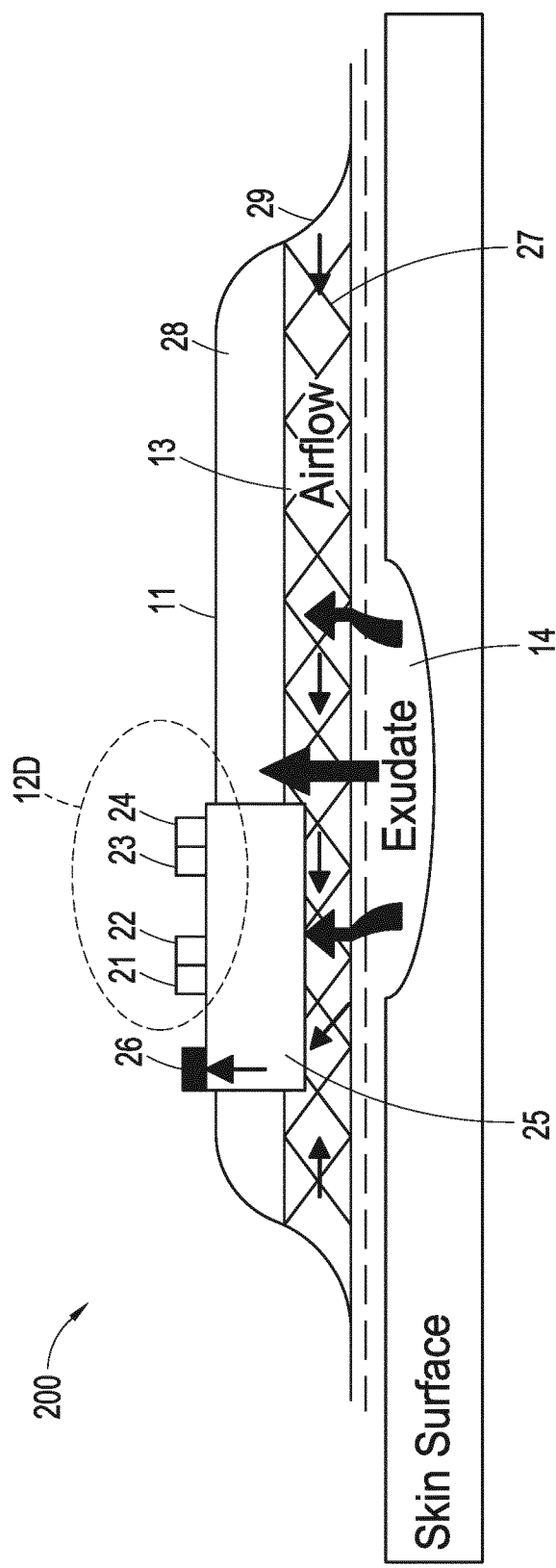
FIGS. 2A and 2B respectively illustrate a side view and top view of a negative pressure therapy system according to some embodiments, such as the negative pressure therapy system of FIG. 1.
Figure 2B:
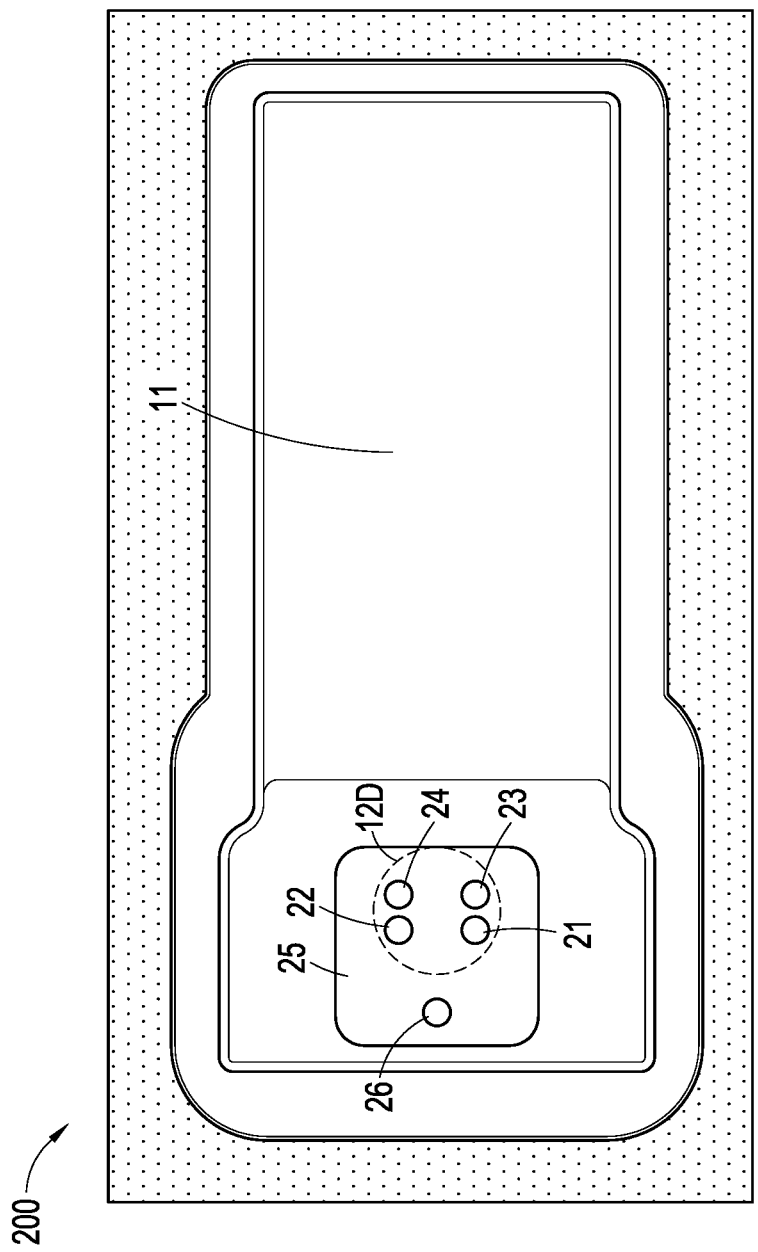

FIG. 2A illustrates a side view of a negative pressure therapy system 200, and FIG. 2B illustrates a top view of the negative pressure therapy system 200. The negative pressure therapy system 200 can be an example implementation of the negative pressure therapy system 100.

In the negative pressure therapy system 200, the wound dressing 13 of the TNP apparatus 11 is shown as attached to the wound 14. Arrows depict the flow of air through the wound dressing 13 and wound exudate from the wound 14. The TNP apparatus 11 can include an air exhaust 26 and a component area 25, such as a components housing or storage area for components of the TNP apparatus 11 like one or more of the control circuitry 12A, memory device 12B, negative pressure source 12C, user interface 12D, power source 12E, first pressure sensor 12F, second pressure sensor 12G, and skin detector 12H.

The user interface 12D of the negative pressure therapy system 200 can include a switch 21 (such as a dome switch), an interface element 22 (such as an electrical contact), a first indicator 23 (such as a first LED), and a second indicator 24 (such as a second LED). The switch 21 can receive a negative pressure activation or deactivation user input (for example, such as receiving the activation or deactivation user input in response to depression of the switch 21 for a period of time, like from between 0.5 seconds and 5 seconds). The interface element 22 can receive a negative pressure disable user input. The first indicator 23 and the second indicator 24 can indicate an operating status like functioning normally, under fault condition, or awaiting user input. In some implementations, the switch 21 or the interface element 22 can couple to a power supply connection of the negative pressure source 12C or the control circuitry 12A (such as a controller of the control circuitry 12A) or an enable signal of the negative pressure source 12C or the control circuitry 12A to activate or deactivate supply of negative pressure or disable supply of negative pressure. Additionally or alternatively, a SMT pin header may be used to activate or deactivate supply of negative pressure or disable supply of negative pressure.

Component parts of the wound dressing 13 of the negative pressure therapy system 200 are illustrated to include an airlock layer 27, an absorbing layer 28, and a contact layer 29. The airlock layer 27 can enable air flow. The absorbing layer 28 can absorb wound exudate. The contact layer 29 can be soft and include silicon and be used to couple the TNP apparatus 11 to the patient.

Figure 3:
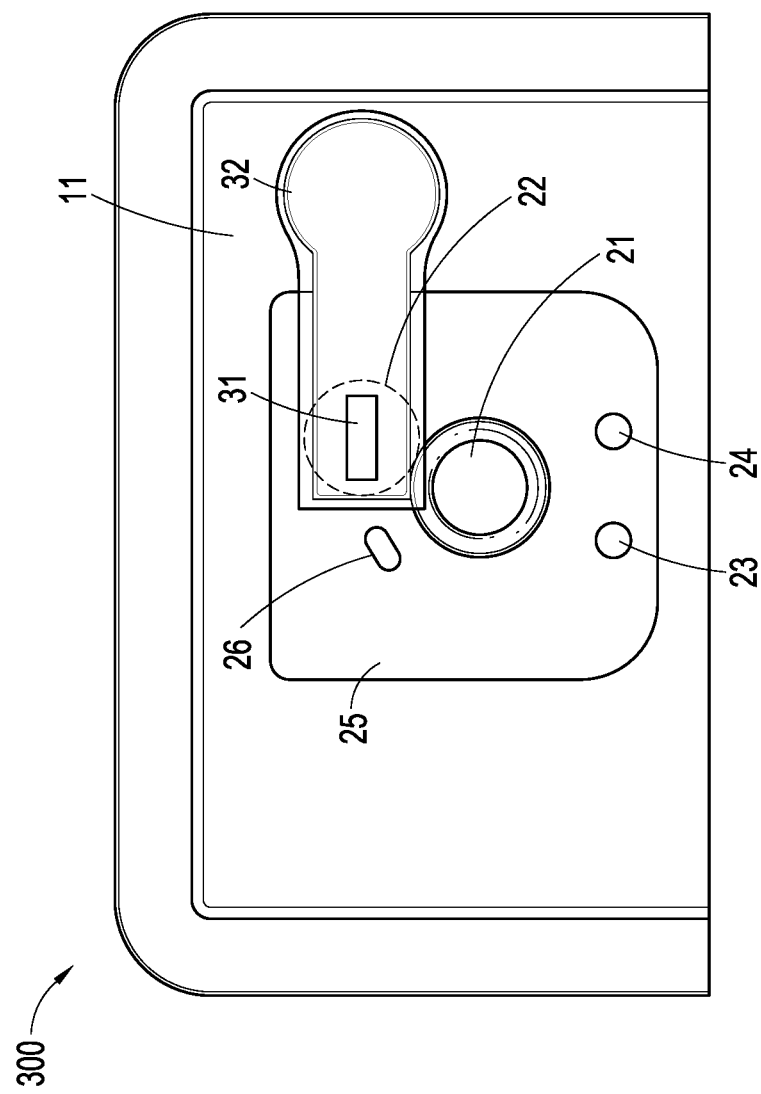

FIG. 3 illustrates a top view of a negative pressure therapy system 300, which can be a more detailed example implementation of the negative pressure therapy system 200. The interface element 22 as shown can include an activating part 31 that may be molded in the film welded at position 32 to the wound dressing 13. The activating part 31 can be used to receive the user input for the interface element 22.

Figure 4:
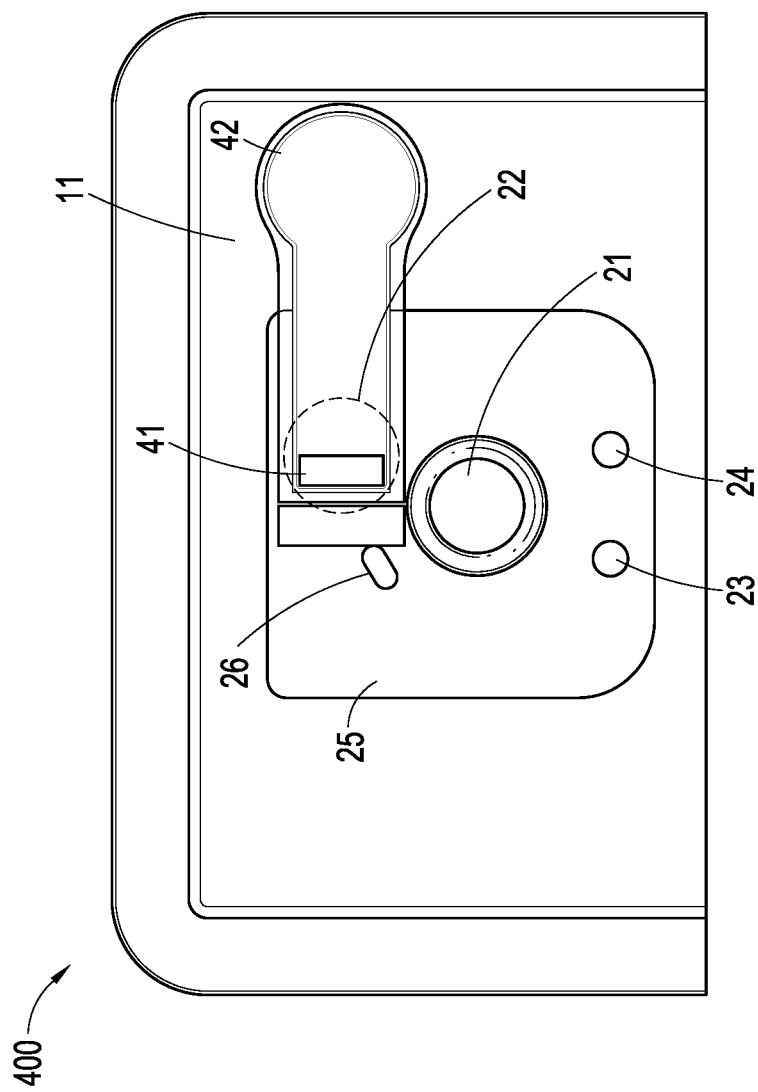

FIG. 4 illustrates a top view of a negative pressure therapy system 400, which can be a more detailed example implementation of the negative pressure therapy system 200. The interface element 22 as shown can include a printed circuit board (PCB) 41 that may be flexible and built into a film for insertion and welded at position 42 to the wound dressing 13. The printed circuit board 41 can be used to receive the user input for the interface element 22. Moreover, the locking mechanism of a zero insertion force (ZIF) connector may be used to improve retention.

Figure 5A:
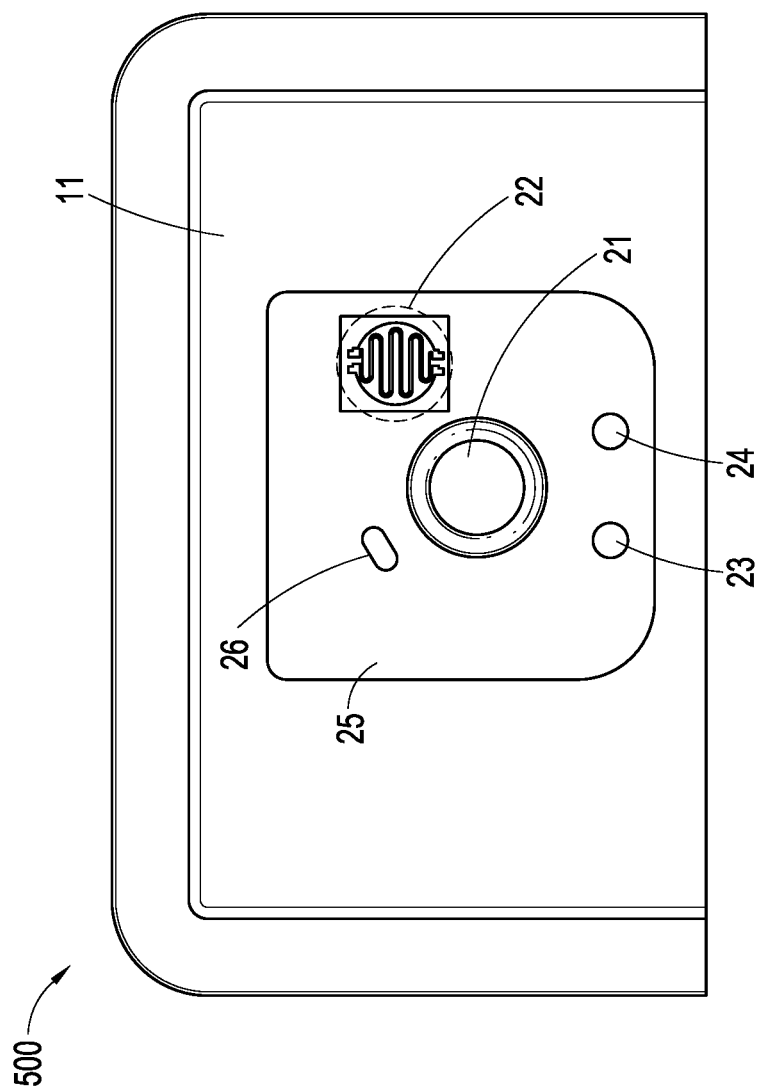

FIGS. 5A and 5B illustrate a top view of a negative pressure therapy system 500, which can be a more detailed example implementation of the negative pressure therapy system 200. The interface element 22 as shown can include a conductive label 51 that can be used to complete an electrical contact when attached (see FIG. 5B) and disconnect the electrical contact upon removal to receive the user input for the interface element 22. Moreover, the locking mechanism of a ZIF connector may be used to improve retention.

Figure 6:
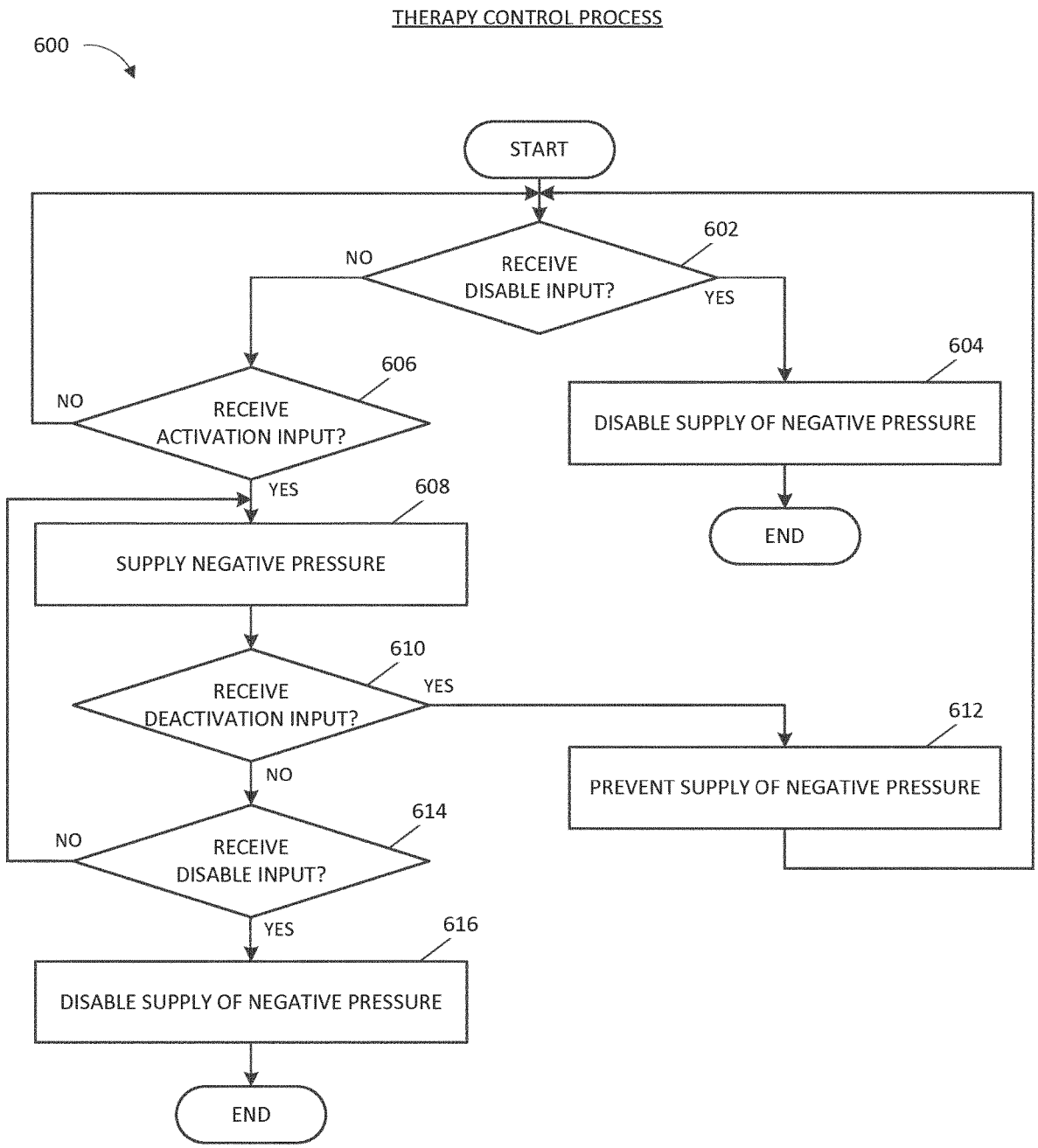
FIG. 6 illustrates a therapy control process performable by a negative pressure therapy system according to some embodiments.

FIG. 6 illustrates a therapy control process 600 usable to control delivery of negative pressure therapy by an apparatus, such as the TNP apparatus 11. For convenience, the therapy control process 600 is described in the context of the TNP apparatus 11, but may instead be implemented in other systems described herein or by other systems not shown. The therapy control process 600 can be performed, in some instances, by the control circuitry 12A of the TNP apparatus 11.

At block 602, the therapy control process 600 can determine whether a disable input was received from a user. The disable input may, for instance, be received from the user via the interface element 22. In some implementations, the disable input may not be provided by any user input to the TNP apparatus 11 other than via the interface element 22.

If the disable input was received, at block 604, the therapy control process 600 can disable supply of negative pressure. The supply of negative pressure can, for instance, be disabled by deactivation of operation of the negative pressure source 12C or the control circuitry 12A, opening of a vent positioned in the fluid flow path, and closing of a valve positioned in the fluid flow path. After block 604, the therapy control process 600 can end. In some implementations, after block 604, the TNP apparatus 11 may no longer be activated by user input to the switch 21, and the user may thus no longer be able to cause the TNP apparatus 11 to generate negative pressure.

If the disable input was not received, at block 606, the therapy control process 600 can determine whether an activation input was received from the user. The activation input may, for instance, be received from the user via the switch 21. In some implementations, the activation input may not be provided by any user input to the TNP apparatus 11 other than via the switch 21.

If the activation input was not received, the therapy control process 600 can return to block 602 and again determine whether the disable input was received from the user.

On the other hand, if the activation input was received, at block 608, the therapy control process 600 can supply negative pressure. The supply of negative pressure can be performed by the negative pressure source 12C, and the negative pressure can be supplied to the wound dressing 13 via the fluid flow path.

At block 610, the therapy control process 600 can determine whether a deactivation input was received from the user. The deactivation input may, for instance, be received from the user via the switch 21. In some implementations, the deactivation input may not be provided by any user input to the TNP apparatus 11 other than via the switch 21.

If the deactivation input was received, at block 612, the therapy control process 600 can prevent the supply of negative pressure. The supply of negative pressure can, for instance, be prevented by one or more of deactivation of operation of the negative pressure source 12C, opening of a vent positioned in the fluid flow path, and closing of a valve positioned in the fluid flow path. After block 612, the therapy control process 600 can return to block 602 and again determine whether the disable input was received from the user.

If the deactivation input was received, at block 614, the therapy control process 600 can determine whether the disable input was received from the user. The disable input may, for instance, be received from the user via the interface element 22. In some implementations, the disable input may not be provided by any user input to the TNP apparatus 11 other than via the interface element 22. In some embodiments, block 614 is periodically executed while the TNP apparatus 11 provides negative pressure wound therapy in order to determine if supply of negative pressure should be disabled.

If the disable input was not received, the therapy control process 600 can return to block 608 and the supply of negative pressure can continue.

If the disable input was received, at block 616, the therapy control process 600 can disable supply of negative pressure. The supply of negative pressure can, for instance, be disabled by deactivation of operation of the negative pressure source 12C or the control circuitry 12A, opening of a vent positioned in the fluid flow path, and closing of a valve positioned in the fluid flow path. After block 616, the therapy control process 600 can end. In some implementations, after block 616, the TNP apparatus 11 may no longer be activated by user input to the switch 21, and the user may thus no longer be able to cause the TNP apparatus 11 to generate negative pressure. Additionally or alternatively, the TNP apparatus 11 may no longer be activated by user input to the switch 21 until an enable input is received, such as from the user via the interface element 22. In some implementations, the enable input may not be provided by any user input to the TNP apparatus 11 other than via the interface element 22.

In some implementations of the therapy control process 600, the supply of negative pressure may not stop by any user inputs other than the deactivation input or the disable input.

FIGS. 7A, 7B, 7C illustrate connectors, which can be used with any of the embodiments of the negative pressure system described herein. FIG. 7A illustrates a header 700A with four circuits (or connectors) 70A, 70B, 70C, and 70D for connecting, for example, the switch 21 and the interface element 22 to each pair of circuits. FIG. 7B illustrates an SMT pin header 700B for connecting, for example, the switch 21 and the interface element 22. In some implementations, the switch 21 can be connected to the connector 72A and the interface element 22 can be connected to the connector 72B or vice versa. FIG. 7C illustrates a ZIF connector 700C having a terminal 74 to which the switch 21 or the interface element 22 can be connected. In some embodiments, two ZIF connectors 700C can be used for connecting each of the switch 21 and interface element 22.

Figure 8A:
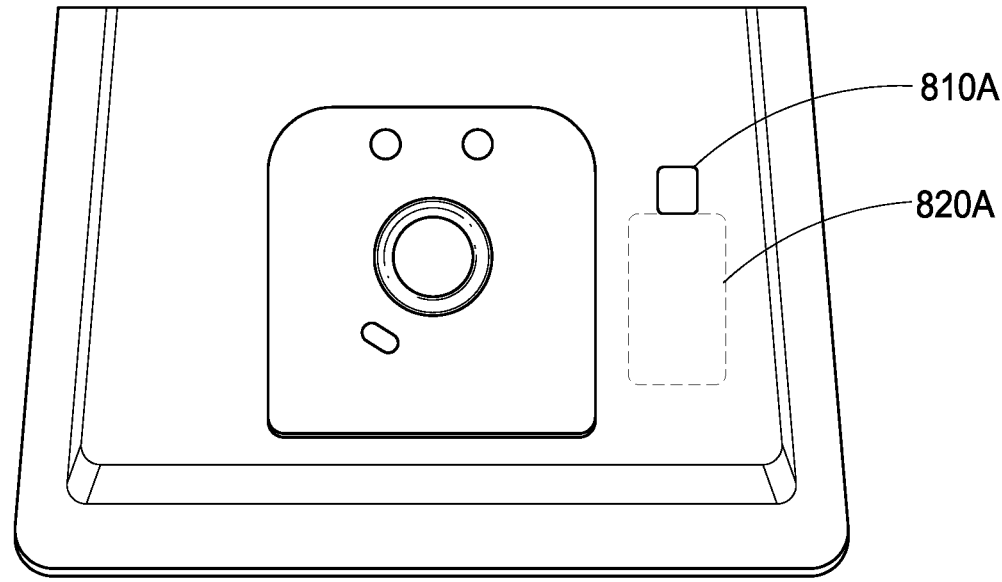
FIGS. 8A and 8B illustrate top views of negative pressure therapy systems according to some embodiments, such as the negative pressure therapy system of FIGS. 2A and 2B.
Figure 8B:
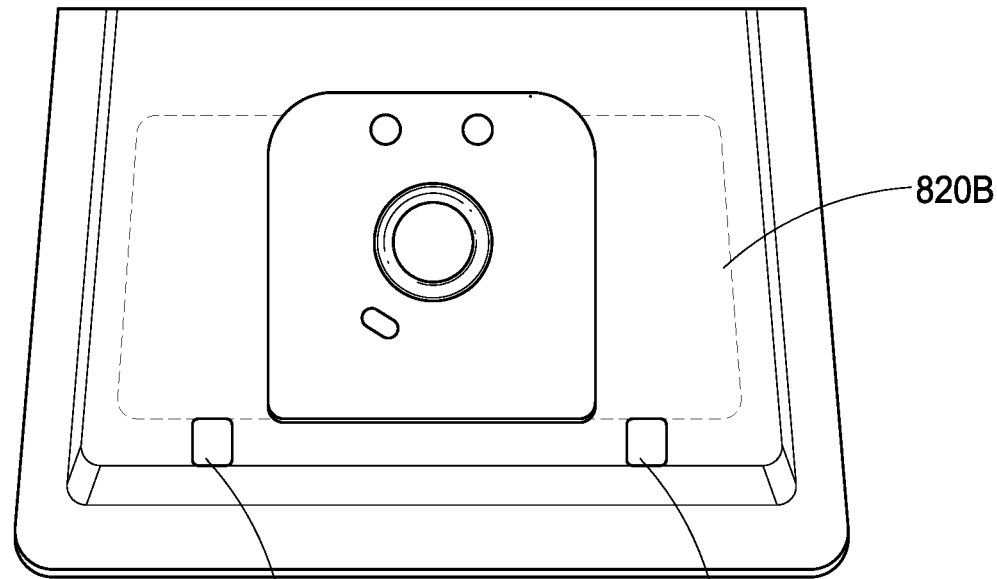

FIG. 8A illustrates a top view of a negative pressure therapy system 800A, which can be a more detailed example implementation of the negative pressure therapy system 200. A tab 810A can be pulled to rip an aperture in the wound dressing to force a gross leak along the dotted line 820A that causes termination of delivery of negative pressure. FIG. 8B illustrates a top view of a negative pressure therapy system 800B, which can be a more detailed example implementation of the negative pressure therapy system 200. Tabs 810B can be pulled to tear the wound dressing along the dotted line 820B to disrupt a power supply or electronics for the TNP apparatus (such as to remove a battery or electrical components) that causes termination of delivery of negative pressure.

Figure 9:
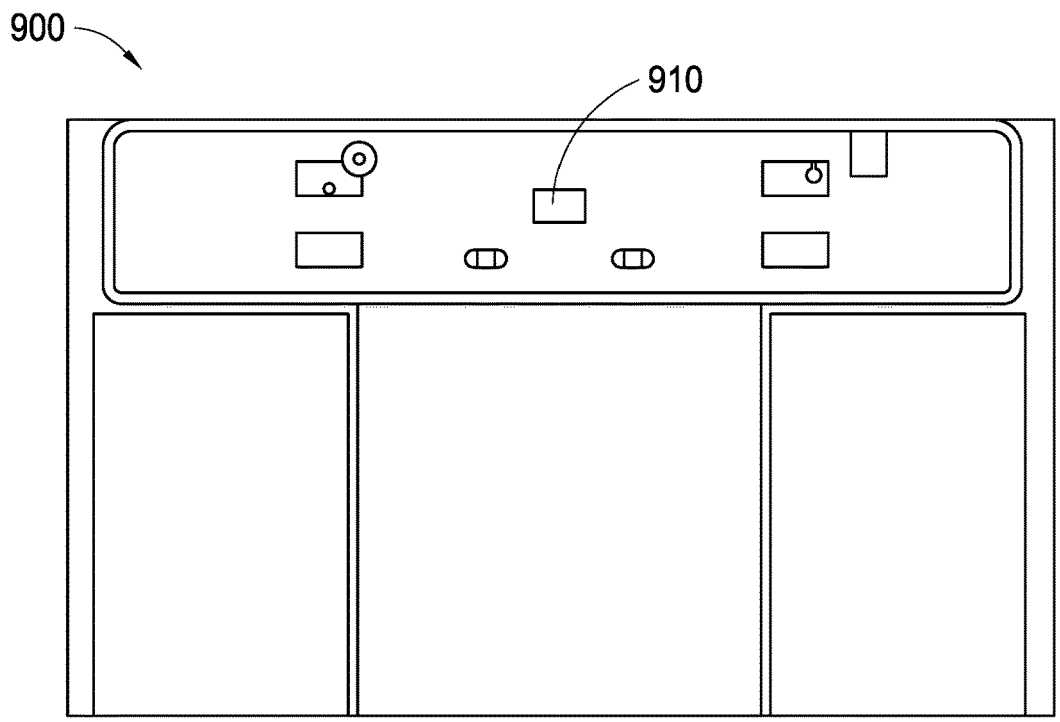
FIGS. 9, 10, 11, and 12 illustrate components of negative pressure therapy systems according to some embodiments, such as the negative pressure therapy system of FIGS. 2A and 2B.

FIG. 9 illustrates components 900 of a negative pressure therapy system, which can be a more detailed example implementation of the negative pressure therapy system 200. The components 900 can illustrate that the batteries can be separated from control electronics, and the connection between the batteries and control electronics can be used as an activation function. The components 900 can include a surface mount connector 910 on an underside as illustrated.

Figure 10:
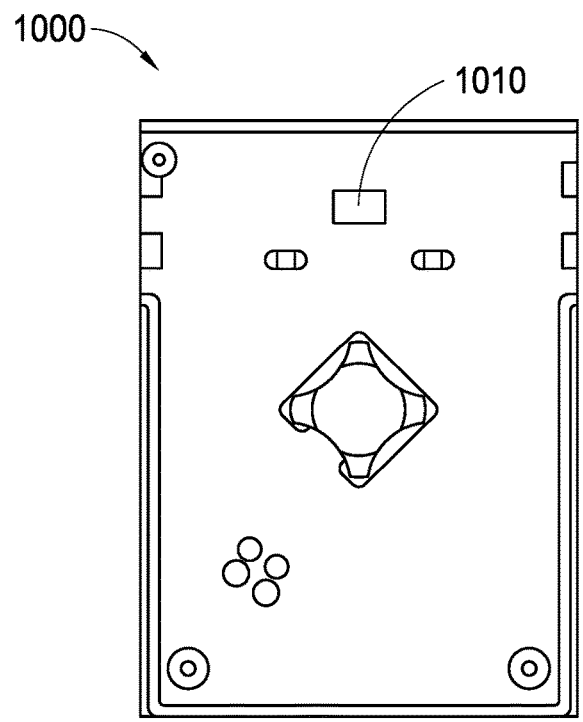

FIG. 10 illustrates components 1000 of a negative pressure therapy system, which can be a more detailed example implementation of the negative pressure therapy system 200. The components 1000 can include a surface mount connector 1010 on an upperside as illustrated. The components 1000 can illustrate that a main electric area can include a rigid PCB and have a connector on an uppermost surface to connect to a battery assembly.

Figure 11:
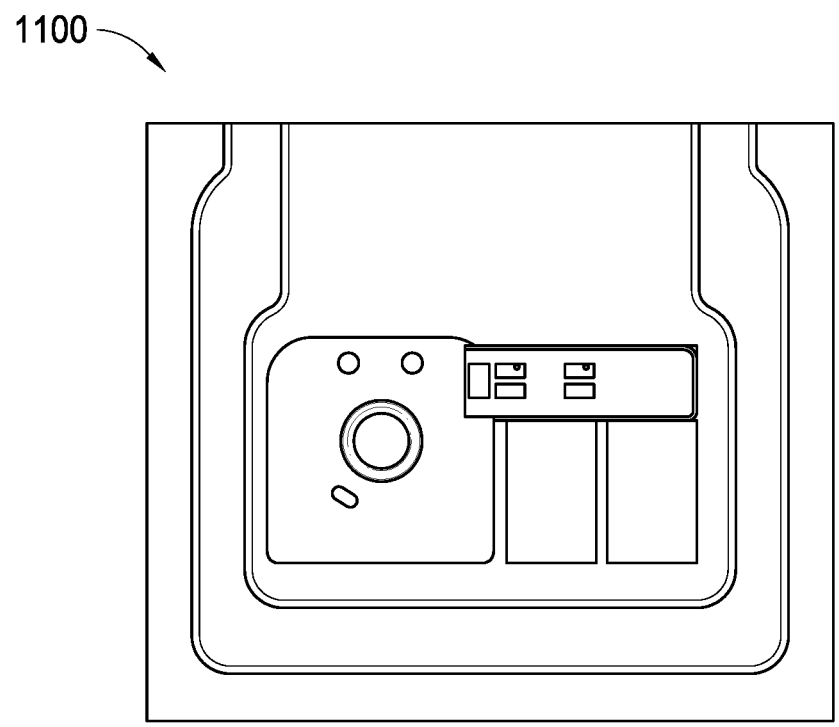

FIG. 11 illustrates components 1100 of a negative pressure therapy system, which can be a more detailed example implementation of the negative pressure therapy system 200. The components 1100 can illustrate an arrangement of repartitioned electronics relative to one or more other embodiments. The pump can be on one side, and batteries can be added as a pack. The pack could have silicone underside to adhere to the wound dressing. The components 1100 can include a surface mount connector on an underside as illustrated.

Figure 12:
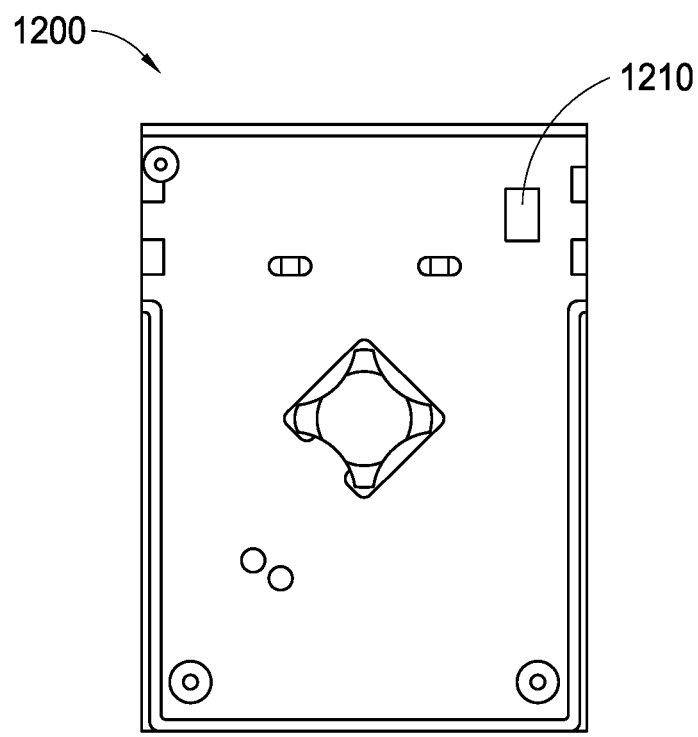

FIG. 12 illustrates components 1200 of a negative pressure therapy system, which can be a more detailed example implementation of the negative pressure therapy system 200.

The components 1200 can illustrate a top of a pump module with a surface mount connector 1210 still on an upperside.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract, and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure to a wound, the apparatus comprising:
   a wound dressing configured to be placed over a wound of a patient;
   a negative pressure source disposed on or within the wound dressing, the negative pressure source configured to supply negative pressure to the wound dressing via a fluid flow path;
   a switch disposed on or within the wound dressing, the switch being configured to receive a first user input to control supply of negative pressure with the negative pressure source;
   an interface element disposed on or within the wound dressing, the interface element being configured to receive a second user input to disable supply of negative pressure with the negative pressure source if the first user input is no longer usable to prevent supply of negative pressure with the negative pressure source; and
   control circuitry electrically coupled to the switch and the interface element, the control circuitry being configured to:
      supply negative pressure with the negative pressure source in response to receipt of the first user input when the negative pressure source is not supplying negative pressure,
      prevent supply of negative pressure with the negative pressure source in response to receipt of the first user input when the negative pressure source is supplying negative pressure, and
      in response to receipt of the second user input, disable supply of negative pressure with the negative pressure source by disconnection of power to the negative pressure source without disconnecting power to the control circuitry.

2. The apparatus of claim 1, wherein when the switch experiences a fault and is no longer able to receive the first user input, the control circuitry is further configured to prevent or disable supply of negative pressure with the negative pressure source in response to receipt of no user inputs other than the second user input.

3. The apparatus of claim 1, wherein the control circuitry is further configured to supply negative pressure with the negative pressure source in response to receipt of no user inputs other than the first user input.

4. The apparatus of claim 1, wherein when the negative pressure source is supplying negative pressure, the control circuitry is further configured to prevent or disable supply of negative pressure with the negative pressure source in response to receipt of no user inputs other than the first user input and the second user input.

5. The apparatus of claim 1, wherein the interface element is configured to receive a third user input to enable supply of negative pressure with the negative pressure source, and subsequent to disabling supply of negative pressure with the negative pressure source, the control circuitry is, in response to receipt of the third user input, further configured to enable supply of negative pressure with the negative pressure source by connection of power to the negative pressure source.

6. The apparatus of claim 1, wherein the control circuitry is configured to prevent supply of negative pressure with the negative pressure source by deactivation of operation of the negative pressure source.

7. The apparatus of claim 1, wherein the control circuitry is configured to prevent supply of negative pressure with the negative pressure source by opening of a vent positioned in the fluid flow path.

8. The apparatus of claim 1, wherein the control circuitry is configured to prevent supply of negative pressure with the negative pressure source by closing of a valve positioned in the fluid flow path.

9. The apparatus of claim 1, wherein the interface element is molded in a film coupled to the wound dressing.

10. The apparatus of claim 1, wherein the interface element comprises an electrical contact configured to receive the second user input.

11. The apparatus of claim 1, wherein the switch is configured to receive the first user input in response to depression of the switch for a period of time.

12. The apparatus of claim 11, wherein the period of time is between 0.5 seconds and 5 seconds.

13. A method of operating a negative pressure wound therapy apparatus comprising a wound dressing, a negative pressure source disposed on or within the wound dressing, a switch disposed on or within the wound dressing, and an interface element disposed on or within the wound dressing, the switch being configured to receive a first user input to control supply of negative pressure with the negative pressure source, the interface element being configured to receive a second user input to disable supply of negative pressure with the negative pressure source if the first user input is no longer usable to prevent supply of negative pressure with the negative pressure source, and control circuitry, the method comprising:
   supplying negative pressure with the negative pressure source to the wound dressing via a fluid flow path in response to receipt of the first user input when the negative pressure source is not supplying negative pressure to the wound dressing;
   preventing supply of negative pressure with the negative pressure source to the wound dressing via the fluid flow path in response to receipt of the first user input when the negative pressure source is supplying negative pressure to the wound dressing;
   in response to receipt of the second user input, disabling supply of negative pressure with the negative pressure source by disconnecting power to the negative pressure source without disconnecting power to the control circuitry.

14. The method of claim 13, further comprising subsequent to the switch experiencing a fault and no longer being able to receive the first user input, preventing or disabling supply of negative pressure with the negative pressure source in response to receipt of no user inputs other than the second user input.

15. The method of claim 13, further comprising supplying negative pressure with the negative pressure source in response to receipt of no user inputs other than the first user input.

16. The method of claim 13, further comprising when the negative pressure source is supplying negative pressure, preventing or disabling supply of negative pressure with the negative pressure source in response to receipt of no user inputs other than the first user input and the second user input.

17. The method of claim 13, wherein said preventing supply of negative pressure with the negative pressure source comprises deactivating operation of the negative pressure source.

18. The method of claim 13, further comprising receiving the second user input via an electrical contact of the interface element.

19. The method of claim 13, further comprising receiving the first user input in response to depression of the switch for a period of time.

20. The method of claim 19, wherein the period of time is between 0.5 seconds and 5 seconds.

* * * * *